(12) United States Patent
McDonald et al.

(10) Patent No.: US 7,699,962 B2
(45) Date of Patent: Apr. 20, 2010

(54) PROCESSES UTILIZING EXTRACTIVE DISTILLATION

(75) Inventors: Michael Francis McDonald, Kingwood, TX (US); Ralph Howard Schatz, Dillon, CO (US); Claude André Gautier, Bois-Guillaume (FR); Richard Dwight Hembree, Zachary, LA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 48 days.

(21) Appl. No.: 11/628,592

(22) PCT Filed: Jun. 23, 2004

(86) PCT No.: PCT/US2004/020164

§ 371 (c)(1),
(2), (4) Date: Dec. 5, 2006

(87) PCT Pub. No.: WO2006/009553

PCT Pub. Date: Jan. 26, 2006

(65) Prior Publication Data

US 2007/0249877 A1    Oct. 25, 2007

(51) Int. Cl.
*C07C 17/386* (2006.01)
*C07C 19/08* (2006.01)

(52) U.S. Cl. .............................. 203/67; 203/57; 203/68; 203/70

(58) Field of Classification Search .................. None
See application file for complete search history.

(56) References Cited

U.S. PATENT DOCUMENTS

| | | | | |
|---|---|---|---|---|
| 2,534,698 A | * | 12/1950 | Calfee et al. ................ 526/206 |
| 2,548,415 A | | 4/1951 | Welch et al. ................ 260/85.3 |
| 2,644,809 A | | 7/1953 | Saylor ........................ 260/85.3 |
| 3,470,143 A | | 9/1969 | Schrage et al. ............. 260/82.5 |
| 5,087,329 A | | 2/1992 | Felix ............................ 203/67 |
| 5,200,431 A | | 4/1993 | Dattani et al. ............... 570/178 |
| 5,417,930 A | | 5/1995 | McDonald, Jr. et al. ...... 422/131 |
| 5,470,442 A | | 11/1995 | Mahler et al. ................. 203/56 |
| 5,527,870 A | | 6/1996 | Maeda et al. .............. 526/348.7 |
| 5,624,878 A | | 4/1997 | Devore et al. ............... 502/152 |
| 5,723,429 A | | 3/1998 | Mahler et al. ............... 510/408 |
| 5,744,662 A | | 4/1998 | Moallemi .................... 570/180 |
| 5,830,325 A | | 11/1998 | Mahler et al. ................. 206/56 |
| 6,156,161 A | | 12/2000 | Miller ........................... 206/67 |
| 6,307,115 B1 | | 10/2001 | Guiraud et al. ............. 570/178 |
| 6,527,917 B1 | | 3/2003 | Kohno et al. ................. 203/67 |
| 2004/0015029 A1 | | 1/2004 | Lange et al. ................. 585/521 |
| 2004/0171772 A1 | | 9/2004 | Huffer et al. .................. 526/64 |

FOREIGN PATENT DOCUMENTS

| | | |
|---|---|---|
| CA | 2337003 | 1/2000 |
| DE | 10154052 | 7/2003 |
| EP | 0472391 | 2/1992 |
| EP | 1003699 | 5/2000 |
| WO | WO 95/24370 | 9/1995 |
| WO | WO 02/34794 | 5/2002 |
| WO | WO 2004/058827 | 7/2004 |
| WO | WO 2004/058828 | 7/2004 |

OTHER PUBLICATIONS

Cationic Polymerization of Olefins: A Critical Inventory, J.P. Kennedy, Wiley Interscience, New York, pp. 10-13 (1975).
Chemical and Engineering News, 63(5), 27 1985.
B, Wunderlich, "The Nature of the Glass Transition and It's Determination by Thermal Analysis", in Assignment of the Glass Transition, ASTM STP 1249, R.J. Seyler, Ed., American Society for Testing and Materials, pp. 17-31, Philadelphia, (1994).
K. Matyjaszewski, ed. Cationic Polymerization, Marcel Dekker, Inc., New York, 1996.
Organic Chemistry, Sixth Edition, Morrison and Boyd, Prentice-Hall, entitled "Ionic Polymerization. Living Polymers", pp. 1084-1085, (Englewood Cliffs New Jersey) 1992.
Research Disclosure "The Use of Azeotrope and Azeotrope-like Blowing Agent Mixtures in Polyurethane Foam", vol. 390, No. 050, Oct. 10, 1996.
W.A. Thaler et al., entitled "High Molecular-Weight, High Unsaturation Copolymers of Isobutylene and Conjugated Dienes", 49(4) Rubber Chemical Technology, 960 (1976).

* cited by examiner

*Primary Examiner*—Daniel M Sullivan
*Assistant Examiner*—Yevegeny Valenrod
(74) *Attorney, Agent, or Firm*—Xiaobing Feng; Nancy T. Krawczyk (57) ABSTRACT

The invention relates to methods for separating mixture components such as reactor effluent components. In particular, the invention relates to the use of an extractive agent such as a hydrocarbon in an extractive distillation process to separate monomers such as a $C_4$-$C_7$ isoolefins such as isobutylene from mixtures such as reactor effluents including one or more hydrofluorocarbon(s) (HFC).

5 Claims, 3 Drawing Sheets

PROCESSES UTILIZING EXTRACTIVE DISTILLATION

CROSS REFERENCE TO RELATED APPLICATIONS

This application is a 371 National Stage Application of International Application No. PCT/US2004/020164, filed Jun. 23, 2006, the disclosures of which are herein incorporated by reference in their entireties.

FIELD OF INVENTION

The invention relates to methods for separating mixture components such as reactor effluent components. In particular, the invention relates to the use of an extractive agent such as a hydrocarbon in an extractive distillation process to separate monomers such as a $C_4$-$C_7$ isoolefins such as isobutylene from mixtures such as reactor effluents including one or more hydrofluorocarbon(s) (HFC).

BACKGROUND

Isoolefin polymers are prepared in carbocationic polymerization processes. The carbocationic polymerization of isobutylene and its copolymerization with comonomers like isoprene is mechanistically complex. See, e.g., *Organic Chemistry*, SIXTH EDITION, Morrison and Boyd, Prentice-Hall, 1084-1085, Englewood Cliffs, N.J. 1992, and K. Matyjaszewski, ed, *Cationic Polymerizations*, Marcel Dekker, Inc., New York, 1996. The catalyst system is typically composed of two components: an initiator and a Lewis acid. Examples of Lewis acids include $AlCl_3$ and $BF_3$. Examples of initiators include Brønsted acids such as HCl, RCOOH (wherein R is an alkyl group), and $H_2O$. During the polymerization process, in what is generally referred to as the initiation step, isobutylene reacts with the Lewis acid/initiator pair to produce a carbenium ion. Following, additional monomer units add to the formed carbenium ion in what is generally called the propagation step. These steps typically take place in a diluent or solvent. Temperature, diluent polarity, and counterions affect the chemistry of propagation. Of these, the diluent is typically considered important.

Industry has generally accepted widespread use of a slurry polymerization process (to produce butyl rubber, polyisobutylene, etc.) in the diluent methyl chloride. Typically, the polymerization process extensively uses methyl chloride at low temperatures, generally lower than −90° C., as the diluent for the reaction mixture. Methyl chloride is employed for a variety of reasons, including that it dissolves the monomers and aluminum chloride catalyst but not the polymer product. Methyl chloride also has suitable freezing and boiling points to permit, respectively, low temperature polymerization and effective separation from the polymer and unreacted monomers. The slurry polymerization process in methyl chloride offers a number of additional advantages in that a polymer concentration of approximately 26% to 37% by volume in the reaction mixture can be achieved, as opposed to the concentration of only about 8% to 12% in solution polymerization. An acceptable relatively low viscosity of the polymerization mass is obtained enabling the heat of polymerization to be removed more effectively by surface heat exchange. Slurry polymerization processes in methyl chloride are used in the production of high molecular weight polyisobutylene and isobutylene-isoprene butyl rubber polymers. Likewise polymerizations of isobutylene and para-methylstyrene are also conducted using methyl chloride. Similarly, star-branched butyl rubber is also produced using methyl chloride.

However, there are a number of problems associated with the polymerization in methyl chloride, for example, the tendency of the polymer particles in the reactor to agglomerate with each other and to collect on the reactor wall, heat transfer surfaces, impeller(s), and the agitator(s)/pump(s). The rate of agglomeration increases rapidly as reaction temperature rises. Agglomerated particles tend to adhere to and grow and plate-out on all surfaces they contact, such as reactor discharge lines, as well as any heat transfer equipment being used to remove the exothermic heat of polymerization, which is critical since low temperature reaction conditions must be maintained.

The commercial reactors typically used to make these rubbers are well mixed vessels of greater than 10 to 30 liters in volume with a high circulation rate provided by a pump impeller. The polymerization and the pump both generate heat and, in order to keep the slurry cold, the reaction system needs to have the ability to remove the heat. An example of such a continuous flow stirred tank reactor ("CFSTR") is found in U.S. Pat. No. 5,417,930, incorporated by reference, hereinafter referred to in general as a "reactor" or "butyl reactor". In these reactors, slurry is circulated through tubes of a heat exchanger by a pump, while boiling ethylene on the shell side provides cooling, the slurry temperature being determined by the boiling ethylene temperature, the required heat flux and the overall resistance to heat transfer. On the slurry side, the heat exchanger surfaces progressively accumulate polymer, inhibiting heat transfer, which would tend to cause the slurry temperature to rise. This often limits the practical slurry concentration that can be used in most reactors from 26 to 37 volume % relative to the total volume of the slurry, diluent, and unreacted monomers. The subject of polymer accumulation has been addressed in several patents (such as U.S. Pat. No. 2,534,698, U.S. Pat. No. 2,548,415, U.S. Pat. No. 2,644,809). However, these patents have unsatisfactorily addressed the myriad of problems associated with polymer particle agglomeration for implementing a desired commercial process.

U.S. Pat. No. 2,534,698 discloses, inter alia, a polymerization process comprising the steps in combination of dispersing a mixture of isobutylene and a polyolefin having 4 to 14 carbon atoms per molecule, into a body of a fluorine substituted aliphatic hydrocarbon containing material without substantial solution therein, in the proportion of from one-half part to 10 parts of fluorine substituted aliphatic hydrocarbon having from one to five carbon atoms per molecule which is liquid at the polymerization temperature and polymerizing the dispersed mixture of isobutylene and polyolefin having four to fourteen carbon atoms per molecule at temperatures between −20° C. and −164° C. by the application thereto a Friedel-Crafts catalyst. However, '698 teaches that the suitable fluorocarbons would result in a biphasic system with the monomer, comonomer and catalyst being substantially insoluble in the fluorocarbon making their use difficult and unsatisfactory.

U.S. Pat. No. 2,548,415 discloses, inter alia, a continuous polymerization process for the preparation of a copolymer, the steps comprising continuously delivering to a polymerization reactors a stream consisting of a major proportion of isobutylene and a minor proportion isoprene; diluting the mixture with from ½ volume to 10 volumes of ethylidene difluoride; copolymerizing the mixture of isobutylene isoprene by the continuous addition to the reaction mixture of a liquid stream of previously prepared polymerization catalyst consisting of boron trifluoride in solution in ethylidene difluoride, maintaining the temperature between −40° C. and −103° C. throughout the entire copolymerization reaction .... '415 teaches the use of boron trifluoride and its complexes as the Lewis acid catalyst and 1,1-difluoroethane as a preferred combination. This combination provides a system in which the catalyst, monomer and comonomer are all soluble and yet still affords a high degree of polymer insolubility to capture the benefits of reduced reactor fouling. However, boron trifluoride is not a preferred commercial catalyst for butyl polymers for a variety of reasons.

U.S. Pat. No. 2,644,809 teaches, inter alia, a polymerization process comprising the steps in combination of mixing together a major proportion of a monoolefin having 4 to 8, inclusive, carbon atoms per molecule, with a minor proportion of a multiolefin having from 4 to 14, inclusive, carbon atoms per molecule, and polymerizing the resulting mixture with a dissolved Friedel-Crafts catalyst, in the presence of from 1 to 10 volumes (computed upon the mixed olefins) of a liquid selected from the group consisting of dichlorodifluoromethane, dichloromethane, trichloromonofluormethane, dichloromonofluormethane, dichlorotetrafluorethane, and mixtures thereof, the monoolefin and multiolefin being dissolved in said liquid, and carrying out the polymerization at a temperature between −20° C. and the freezing point of the liquid. '809 discloses the utility of chlorofluorocarbons at maintaining ideal slurry characteristics and minimizing reactor fouling, but teaches the incorporation of diolefin (i.e. isoprene) by the addition of chlorofluorocarbons (CFC). CFC's are known to be ozone-depleting chemicals. Governmental regulations, however, tightly controls the manufacture and distribution of CFC's making these materials unattractive for commercial operation.

Additionally, Thaler, W. A., Buckley, Sr., D. J., *High Molecular-Weight, High Unsaturation Copolymers of Isobutylene and Conjugated Dienes*, 49(4) Rubber Chemical Technology, 960 (1976), discloses, inter alia, the cationic slurry polymerization of copolymers of isobutylene with isoprene (butyl rubber) and with cyclopentadiene in heptane.

Other general background references include WO 02/34794, WO 02/096964, WO 00/04061, DE 100 61 727 A, U.S. Pat. Nos. 5,624,878, 5,527,870, and 3,470,143.

Therefore, finding alternative diluents or blends of diluents to create new polymerization systems that would reduce particle agglomeration and/or reduce the amount of chlorinated hydrocarbons such as methyl chloride is desirable.

Hydrofluorocarbons (HFCs) are of interest and are currently used as environmentally friendly refrigerants because they have a very low (even zero) ozone depletion potential. Their low ozone depletion potential is thought to be related to the lack of chlorine. The HFCs also typically have low flammability particularly as compared to hydrocarbons and chlorinated hydrocarbons.

However, the use of HFCs in polymerization processes would require finding new post-polymerization or "downstream" processes that would accommodate for such new technology.

Among such post-polymerization or "downstream" processes are methods for separating reactor effluent components after polymerization. In particular, post-polymerization reactor effluents may contain components that need to be removed before the reactor effluent may be recycled to the polymerization process. For example, unreacted monomers may form an azeotropic mixture or azeotrope-like mixture with diluent components such as HFCs.

Azeotropic mixtures or azeotrope-like mixtures involving HFCs in other areas have been encountered in the past. See, e.g., U.S. Pat. Nos. 5,087,329, 5,200,431, 5,470,442, 5,723, 429, 5,744,662, 5,830,325, 6,156,161, 6,307,115, 6,527,917, and EP 1 003 699 B.

In contrast, in conventional butyl rubber polymerization, isobutylene and methyl chloride do not form an azeotrope, and thus can be separated easily by conventional distillation. It has been found, however, that both 1,1,1,2 tetrafluoroethane ("R134a") and 1,1 difluoroethane ("R152a") form maximum boiling azeotropes with isobutylene. Thus, the recovery of certain HFCs without post polymerization unreacted monomers such as isobutylene by simple distillation is not possible.

Post polymerization reactor effluents having HFCs and isobutylene are not usable as carriers for the catalyst system due to the polymerization of contained isobutylene before entry to the reactor and to the deleterious effects this has on catalyst system quality. Thus, it is essential to have a method for recovering the HFCs or at least a portion of the HFC from the post-polymerization reactor effluent before it may be recycled as a diluent into the polymerization process.

Therefore, finding new methods to separate post-polymerization reactor effluent components such as unreacted monomers such as isobutylene is desirable.

SUMMARY OF THE INVENTION

The invention provides for methods for separating mixture components such as reactor effluent components. In particular, the invention provides for methods using an extractive agent such as a hydrocarbon in an extractive distillation process to separate monomers such as isobutylene from mixtures such as reactor effluents including one or more hydrofluorocarbon(s) (HFC).

Additionally, an extractive distillation systems and process can be used to separate isobutylene from R134a or R152a using an extractive agent such as a hydrocarbon such as hexane or a mixture of hexane isomers.

In an embodiment, the invention provides for a method comprising contacting an extractive agent with a mixture, the mixture comprising at least one monomer and a diluent comprising one or more hydrofluorocarbon(s), to form a contact product.

In the previous embodiments, subsequent to contacting with the extractive agent, the contact product may be essentially free of the at least one monomer.

In the previous embodiments, subsequent to contacting with the extractive agent, the contact product may comprise from less than 100 wppm of the at least one monomer.

In the previous embodiments, subsequent to contacting with the extractive agent, the contact product may comprise from less than 30 wppm of the at least one monomer.

In the previous embodiments, subsequent to contacting with the extractive agent, the contact product may comprise from less than 5 wppm of the at least one monomer.

In the previous embodiments, subsequent to contacting with the extractive agent, the contact product may comprise from less than 2 wppm of the at least one monomer.

In the previous embodiments, subsequent to contacting with the extractive agent, the contact product may be free of the at least one monomer.

In the previous embodiments, the extractive agent may comprise at least one hydrocarbon.

In the previous embodiments, the at least one hydrocarbon may comprise at least one alkane.

In the previous embodiments, the at least one alkane may comprise hexane, heptane, or mixtures thereof.

In the previous embodiments, the hexane may comprise n-hexane and/or mixtures of hexane isomers.

In any of the previous embodiments, the ratio of the extractive agent to the diluent is from about 0.2:1.0 to about 1.0:0.2 on a molar basis.

In any of the previous embodiments, the ratio of the extractive agent to the diluent is from about 0.3:1.0 to about 1.0:0.3 on a molar basis.

In any of the previous embodiments, the ratio of the extractive agent to the diluent is from about 0.5:1.0 to about 1.0:0.5 on a molar basis.

In any of the previous embodiments, the ratio of the extractive agent to the diluent is from about 0.7:1.0 to about 1.0:0.7 on a molar basis.

In any of the previous embodiments, the extraction agent has a volatility equivalent to hexane.

In any of the previous embodiments, the at least one monomer is a $C_4$-$C_7$ isoolefin.

In the previous embodiment, the $C_4$-$C_7$ isoolefin is isobutylene.

In any of the previous embodiments, the mixture is a reactor effluent.

In any of the previous embodiments, the mixture is an azeotrope-like mixture.

In any of the previous embodiments, the mixture is an azeotropic mixture.

The extractive distillation process may involve a two column arrangement wherein the extraction of unreacted monomers such as isobutylene takes place in a first column and the purification of the extractive agent takes place in a second column.

The extractive distillation process may alternatively involve a one column arrangement wherein both the extraction of the unreacted monomer and the purification of the extractive agent takes place in a single column. In an embodiment, the extractive distillation system comprises one column, at least one condensing exchanger, and at least one vaporizing exchanger.

The invention also provides for an azeotropic mixture comprising 1,1,1,2 tetrafluoroethane and isobutylene at about 0.84 mole fraction 1,1,1,2 tetrafluoroethane at about 25° C. and at about 0.88 mole fraction 1,1,1,2 tetrafluoroethane at about 75° C.

In yet another embodiment, the invention provides for an azeotrope-like mixture comprising 1,1,1,2 tetrafluoroethane and isobutylene in the range from about 0.750 to about 0.999 mole fraction 1,1,1,2 tetrafluoroethane at about 25° C. and about 75° C.

In yet another embodiment, the invention provides for an azeotropic mixture comprising 1,1 difluoroethane and isobutylene at about 0.87 mole fraction 1,1 difluoroethane at about 25° C. and at about 0.94 mole fraction 1,1 difluoroethane at about 75° C.

In yet another embodiment, the invention provides for an azeotrope-like mixture comprising 1,1 difluoroethane and isobutylene in the range from about 0.750 to about 0.999 mole fraction 1,1 difluoroethane at about 25° C. and about 75° C.

BRIEF DESCRIPTION OF THE DRAWINGS

FIG. 3 shows a plot of the vapor pressure of mixtures of 1,1,1,2 tetrafluoroethane (134a) and isobutylene over the entire range of compositions from 0 to 1.0 mole fraction R134a.

FIG. 4 shows a plot of the vapor pressure of mixtures of 1,1 difluoroethane (152a) and isobutylene over the entire range of compositions from 0 to 1.0 mole fraction R152a.

DETAILED DESCRIPTION

Various specific embodiments, versions and examples of the invention will now be described, including preferred embodiments and definitions that are adopted herein for purposes of understanding the claimed invention. For determining infringement, the scope of the "invention" will refer to any one or more of the appended claims, including their equivalents, and elements or limitations that are equivalent to those that are recited.

For purposes of this invention and the claims thereto the term catalyst system refers to and includes any Lewis acid(s) or other metal complex(es) used to catalyze the polymerization of the olefinic monomers of the invention, as well as at least one initiator, and optionally other minor catalyst component(s).

In one embodiment, the invention provides a polymerization medium suitable to polymerize one or more monomer(s) to form a polymer, the polymerization medium comprising one or more Lewis acid(s), one or more initiator(s), and a diluent comprising one or more hydrofluorocarbon(s) (HFC's).

In another embodiment, the invention provides a polymerization medium suitable to polymerize one or more monomer(s) to form a polymer, the polymerization medium comprising one or more Lewis acid(s) and a diluent comprising one or more hydrofluorocarbon(s) (HFC); wherein the one or more Lewis acid(s) is not a compound represented by formula $MX_3$, where M is a group 13 metal and X is a halogen.

The phrase "suitable to polymerize monomers to form a polymer" relates to the selection of polymerization conditions and components, well within the ability of those skilled in the art necessary to obtain the production of a desired polymer in light of process parameters and component properties described herein. There are numerous permutations of the polymerization process and variations in the polymerization components available to produce the desired polymer attributes. In preferred embodiments, such polymers include polyisobutylene homopolymers, isobutylene-isoprene (butyl rubber) copolymers, isobutylene and para-methylstyrene copolymers, and star-branched butyl rubber terpolymers.

Reactor effluent refers to any gas, vapor, liquid, or combination thereof of the slurry after polymerization and after the precipitated polymer has been separated and recovered with the exception of very minor amount of polymer particles that may be present in the reactor effluent. The reactor effluent includes the diluent or mixture of diluents, the unreacted monomers, as well as other components in the feed or catalyst systems that are not removed with the polymer. Of course, the catalyst system or catalyst system components are present only to the extent they are present after polymerization.

Diluent means a diluting or dissolving agent. Diluent is specifically defined to include chemicals that can act as solvents for the Lewis Acid, other metal complexes, initiators, monomers or other additives. In the practice of the invention, the diluent does not alter the general nature of the components of the polymerization medium, i.e., the components of the catalyst system, monomers, etc. However, it is recognized that interactions between the diluent and reactants may occur. In preferred embodiments, the diluent does not react with the catalyst system components, monomers, etc. to any appreciable extent. Additionally, the term diluent includes mixtures of at least two or more diluents.

A reactor is any container(s) in which a chemical reaction occurs.

Slurry refers to the mixture of diluent comprising polymers that have precipitated from the diluent, unreacted monomers, and a catalyst system and/or catalyst system components. The slurry concentration is the volume percent of the partially or completely precipitated polymers based on the total volume of the slurry.

Azeotrope or azeotropic composition or mixture refers to a constant boiling liquid admixture of two or more chemical substances. One way to characterize an azeotropic composition or mixture is that the vapor produced by partial evaporation or distillation of the liquid has the same composition as the liquid from which it was evaporated or distilled, e.g., the admixture evaporates or distills/refluxes without compositional change. Constant boiling compositions are characterized as azeotropic because they exhibit either a maximum or minimum boiling point, as compared with that of the non-azeotropic mixtures of the same components. An azeotropic composition may also refer to maximum or minimum vapor pressure for a mixture at a given temperature when plotted as a function of mole fraction.

Azeotrope-like composition or mixture refers to a constant boiling, or substantially constant boiling, liquid admixture of two or more chemical substances. In an embodiment, an azeotrope-like composition refers to the vapor produced by partial evaporation or distillation of the liquid having substantially the same composition as the liquid from which it was evaporated or distilled, e.g., the admixture evaporates or distills/refluxes without substantial compositional change. An azeotrope-like composition may also refer to the region which is shown by plotting vapor pressure at given temperature as a function of mole fraction, where the vapor pressure is constant or nearly constant over a range of component compositions.

Extractive agent refers to a higher boiling solvent that is added to the azeotropic mixture or azeotrope-like mixture to alter the relative volatilities of the components. The choice of extractive agent is made to avoid the formation of additional azeotropes or the like and allows separation of the components of the original constant boiling mixture. In embodiment, the extractive agent refers to any material that can separate diluent components from at least one monomer as described in more detail herein.

As used herein, the new numbering scheme for the Periodic Table Groups are used as in CHEMICAL AND ENGINEERING NEWS, 63(5), 27 (1985).

Polymer may be used to refer to homopolymers, copolymers, interpolymers, terpolymers, etc. Likewise, a copolymer may refer to a polymer comprising at least two monomers, optionally with other monomers.

When a polymer is referred to as comprising a monomer, the monomer is present in the polymer in the polymerized form of the monomer or in the derivative form of the monomer. Likewise, when catalyst components are described as comprising neutral stable forms of the components, it is well understood by one skilled in the art, that the ionic form of the component is the form that reacts with the monomers to produce polymers.

Isobutylene-based polymer refers to polymers comprising at least 80 mol % repeat units from isobutylene.

Isoolefin refers to any olefin monomer having two substitutions on the same carbon.

Multiolefin refers to any monomer having more than one double bond. In a preferred embodiment, the multiolefin is any monomer comprising two conjugated double bonds such as isoprene.

Elastomer or elastomeric composition, as used herein, refers to any polymer or composition of polymers consistent with the ASTM D1566 definition. The terms may be used interchangeably with the term "rubber(s)", as used herein.

Alkyl refers to a paraffinic hydrocarbon group which may be derived from an alkane by dropping one or more hydrogens from the formula, such as, for example, a methyl group ($CH_3$), or an ethyl group ($CH_3CH_2$), etc.

Aryl refers to a hydrocarbon group that forms a ring structure characteristic of aromatic compounds such as, for example, benzene, naphthalene, phenanthrene, anthracene, etc., and typically possess alternate double bonding ("unsaturation") within its structure. An aryl group is thus a group derived from an aromatic compound by dropping one or more hydrogens from the formula such as, for example, phenyl, or $C_6H_5$.

Substituted refers to replacement of at least one hydrogen group by at least one substituent selected from, for example, halogen (chlorine, bromine, fluorine, or iodine), amino, nitro, sulfoxy (sulfonate or alkyl sulfonate), thiol, alkylthiol, and hydroxy; alkyl, straight or branched chain having 1 to 20 carbon atoms which includes methyl, ethyl, propyl, tert-butyl, isopropyl, isobutyl, etc.; alkoxy, straight or branched chain alkoxy having 1 to 20 carbon atoms, and includes, for example, methoxy, ethoxy, propoxy, isopropoxy, butoxy, isobutoxy, secondary butoxy, tertiary butoxy, pentyloxy, isopentyloxy, hexyloxy, heptryloxy, octyloxy, nonyloxy, and decyloxy; haloalkyl, which means straight or branched chain alkyl having 1 to 20 carbon atoms which is substituted by at least one halogen, and includes, for example, chloromethyl, bromomethyl, fluoromethyl, iodomethyl, 2-chloroethyl, 2-bromoethyl, 2-fluoroethyl, 3-chloropropyl, 3-bromopropyl, 3-fluoropropyl, 4-chlorobutyl, 4-fluorobutyl, dichloromethyl, dibromomethyl, difluoromethyl, diiodomethyl, 2,2-dichloroethyl, 2,2-dibromomethyl, 2,2-difluoroethyl, 3,3-dichloropropyl, 3,3-difluoropropyl, 4,4-dichlorobutyl, 4,4-difluorobutyl, trichloromethyl, 4,4-difluorobutyl, trichloromethyl, trifluoromethyl, 2,2,2-trifluoroethyl, 2,3,3-trifluoropropyl, 1,1,2,2-tetrafluoroethyl, and 2,2,3,3-tetrafluoropropyl. Thus, for example, a "substituted styrenic unit" includes p-methylstyrene, p-ethylstyrene, etc.

In one embodiment, this invention relates to the use of hydrofluorocarbon(s) or blends of hydrofluorocarbon(s) with hydrocarbon(s) and/or chlorinated hydrocarbon(s) to produce a polymer slurry which is less prone to fouling (i.e., also observed more glass like, less sticky particles in the reaction vessel with reduced adherence to the walls of the vessel or to the stirring impeller as well as reduced particle to particle agglomeration). More particularly, this invention relates to the use of hydrofluorocarbon diluent(s) or HFC diluent blends with hydrocarbons and/or chlorinated hydrocarbon blends to polymerize and copolymerize isoolefins with dienes and/or alkylstyrenes to produce isoolefin homopolymers and copolymers with significantly reduced reactor fouling. Further, this invention relates to the use of hydrofluorocarbon diluent(s) or diluent blends with hydrocarbons and/or chlorinated hydrocarbon blends to polymerize and copolymerize isoolefins with dienes to produce isoolefin copolymers with significantly reduced reactor fouling and hence longer run life for the reactors, as compared to conventional systems.

In one embodiment, this invention relates to the discovery of new polymerization systems using diluents containing hydrofluorocarbons. These diluents effectively dissolve the selected catalyst system and monomers but are relatively poor solvents for the polymer product. Polymerization systems using these diluents are less prone to fouling due to the agglomeration of polymer particles to each other and their depositing on polymerization hardware. In addition, this invention further relates to the use of these diluents in polymerization systems for the preparation of high molecular weight polymers and copolymers at equivalent to or higher than to those polymerization temperatures using solely chlorinated hydrocarbon diluents such as methyl chloride.

In another embodiment, this invention relates to the discovery of new polymerization systems using fluorinated aliphatic hydrocarbons capable of dissolving the catalyst system. These polymerization systems are also beneficial for isoolefin slurry polymerization and production of a polymer slurry that is less prone to fouling, while permitting dissolution of monomer, comonomer and the commercially preferred alkylaluminum halide catalysts. In addition, this invention further relates to the use of these diluents for the preparation of high molecular weight polymers and copolymers at higher polymerization temperatures as compared to polymerization systems using solely chlorinated hydrocarbon diluents such as methyl chloride.

In yet another embodiment, this invention relates to the preparation of isoolefinic homopolymers and copolymers, especially the polymerization reactions required to produce the isobutylene-isoprene form of butyl rubber and isobutylene-p-alkylstyrene copolymers. More particularly, the invention relates to a method of polymerizing and copolymerizing isoolefins in a slurry polymerization process using hydrofluorocarbon diluents or blends of hydrofluorocarbons, and chlorinated hydrocarbon diluents, like methyl chloride.

In another embodiment, the polymerization systems of the present invention provide for copolymerizing an isomonoolefin having from 4 to 7 carbon atoms and para-alkylstyrene monomers. In accordance with a preferred embodiment of the invention, the system produces copolymers containing between about 80 and 99.5 wt. % of the isoolefin such as isobutylene and between about 0.5 and 20 wt. % of the para-alkylstyrene such as para-methylstyrene. In accordance with another embodiment, however, where glassy or plastic materials are being produced as well, the copolymers are comprised between about 10 and 99.5 wt. % of the isoolefin, or isobutylene, and about 0.5 and 90 wt. % of the para-alkylstyrene, such as para-methylstyrene.

In a preferred embodiment this invention relates to a process to produce polymers of cationically polymerizable monomer(s) comprising contacting, in a reactor, the monomer(s), a Lewis acid, and an initiator, in the presence of an HFC diluent at a temperature of 0° C. or lower, preferably −10° C. or lower, preferably −20° C. or lower, preferably −30° C. or lower, preferably −40° C. or lower, preferably −50° C. or lower, preferably −60° C. or lower, preferably −70° C. or lower, preferably −80° C. or lower, preferably −90° C. or lower, preferably −100° C. or lower, preferably from 0° C. to the freezing point of the polymerization medium, such as the diluent and monomer mixture.

Monomers and Polymers

Monomers which may be polymerized by this system include any hydrocarbon monomer that is polymerizable using this invention. Preferred monomers include one or more of olefins, alpha-olefins, disubstituted olefins, isoolefins, conjugated dienes, non-conjugated dienes, styrenics and/or substituted styrenics and vinyl ethers. The styrenic may be substituted (on the ring) with an alkyl, aryl, halide or alkoxide group. Preferably, the monomer contains 2 to 20 carbon atoms, more preferably 2 to 9, even more preferably 3 to 9 carbon atoms. Examples of preferred olefins include styrene, para-alkylstyrene, para-methylstyrene, alpha-methyl styrene, divinylbenzene, diisopropenylbenzene, isobutylene, 2-methyl-1-butene, 3-methyl-1-butene, 2-methyl-2-pentene, isoprene, butadiene, 2,3-dimethyl-1,3-butadiene, 3-pinene, myrcene, 6,6-dimethyl-fulvene, hexadiene, cyclopentadiene, piperylene, methyl vinyl ether, ethyl vinyl ether, and isobutyl vinyl ether and the like. Monomer may also be combinations of two or more monomers. Styrenic block copolymers may also be used a monomers. Preferred block copolymers include copolymers of styrenics, such as styrene, para-methylstyrene, alpha-methylstyrene, and $C_4$ to $C_{30}$ diolefins, such as isoprene, butadiene, and the like. Particularly preferred monomer combinations include 1) isobutylene and para-methyl styrene 2) isobutylene and isoprene, as well as homopolymers of isobutylene.

Additionally, preferred monomers include those that are cationically polymerizable as described in *Cationic Polymerization of Olefins, A Critical Inventory*, Joseph Kennedy, Wiley Interscience, New York 1975. Monomers include any monomer that is cationically polymerizable, such as those monomers that are capable of stabilizing a cation or propagating center because the monomer contains an electron donating group. For a detailed discussion of cationic catalysis please see *Cationic Polymerization of Olefins, A Critical Inventory*, Joseph Kennedy, Wiley Interscience, New York 1975.

The monomers may be present in the polymerization medium in an amount ranging from 75 wt % to 0.01 wt % in one embodiment, alternatively 60 wt % to 0.1 wt %, alternatively from 40 wt % to 0.2 wt %, alternatively 30 to 0.5 wt %, alternatively 20wt % to 0.8 wt %, alternatively and from 15 wt % to 1 wt % in another embodiment.

Preferred polymers include homopolymers of any of the monomers listed in this Section. Examples of homopolymers include polyisobutylene, polypara-methylstyrene, polyisoprene, polystyrene, polyalpha-methylstyrene, polyvinyl ethers (such as polymethylvinylether, polyethylvinylether).

Preferred polymers also include copolymers of 1) isobutylene and an alkylstyrene; and 2) isobutylene and isoprene.

In one embodiment butyl polymers are prepared by reacting a comonomer mixture, the mixture having at least (1) a $C_4$ to $C_6$ isoolefin monomer component such as isobutene with (2) a multiolefin, or conjugated diene monomer component. The isoolefin is in a range from 70 to 99.5 wt % by weight of the total comonomer mixture in one embodiment, 85 to 99.5 wt % in another embodiment. In yet another embodiment the isoolefin is in the range of 92 to 99.5 wt %. The conjugated diene component in one embodiment is present in the comonomer mixture from 30 to 0.5 wt % in one embodiment, and from 15 to 0.5 wt % in another embodiment. In yet another embodiment, from 8 to 0.5 wt % of the comonomer mixture is conjugated diene. The $C_4$ to $C_6$ isoolefin may be one or more of isobutene, 2-methyl-1-butene, 3-methyl-1-butene, 2-methyl-2-butene, and 4-methyl-1-pentene. The multiolefin may be a $C_4$ to $C_{14}$ conjugated diene such as isoprene, butadiene, 2,3-dimethyl-1,3-butadiene, β-pinene, myrcene, 6,6-dimethyl-fulvene, hexadiene, cyclopentadiene and piperylene. One embodiment of the butyl rubber polymer of the invention is obtained by reacting 85 to 99.5 wt % of isobutylene with 15 to 0.5 wt % isoprene, or by reacting 95 to 99.5 wt % isobutylene with 5.0 wt % to 0.5 wt % isoprene in yet another embodiment. The following table illustrates how the above-referenced wt % would be expressed as mol %.

| wt % IC4[a] | mol % IC4 | wt % IC5[b] | Mol % IC5 |
|---|---|---|---|
| 70 | 73.9 | .5 | .4 |
| 85 | 87.3 | 5 | 4.2 |
| 92 | 93.3 | 8 | 6.7 |
| 95 | 95.9 | 15 | 12.7 |
| 99.5 | 99.6 | 30 | 26.1 |

[a]IC4 - isobutylene
[b]IC5 - isoprene

This invention further relates to terpolymers and tetrapolymers comprising any combination of the monomers listed above. Preferred terpolymers and tetrapolymers include polymers comprising isobutylene, isoprene and divinylbenzene, polymers comprising isobutylene, para-alkylstyrene (preferably paramethyl styrene) and isoprene, polymers comprising cyclopentadiene, isobutylene, and paraalkyl styrene (preferably paramethyl styrene), polymers of isobutylene cyclopentadiene and isoprene, polymers comprising cyclopentadiene, isobutylene, and methyl cyclopentadiene, polymers comprising isobutylene, paramethylstyrene and cyclopentadiene.

Lewis Acid

The Lewis acid (also referred to as the co-initiator or catalyst) may be any Lewis acid based on metals from Group 4, 5, 13, 14 and 15 of the Periodic Table of the Elements, including boron, aluminum, gallium, indium, titanium, zirconium, tin, vanadium, arsenic, antimony, and bismuth. One skilled in the art will recognize that some elements are better suited in the practice of the invention. In one embodiment, the metals are aluminum, boron and titanium, with aluminum being desirable. Illustrative examples include $AlCl_3$, (alkyl)$AlCl_2$, $(C_2H_5)_2AlCl$ and $(C_2H_5)_3Al_2Cl_3$, $BF_3$, $SnCl_4$, $TiCl_4$.

Additionally, Lewis acids may be any of those useful in cationic polymerization of isobutylene copolymers including: aluminum trichloride, aluminum tribromide, ethylaluminum dichloride, ethylaluminum sesquichloride, diethylaluminum chloride, methylaluminum dichloride, methylaluminum sesquichloride, dimethylaluminum chloride, boron trifluoride, titanium tetrachloride, etc. with ethylaluminum dichloride and ethylaluminum sesquichloride being preferred.

Lewis acids such as methylaluminoxane (MAO) and specifically designed weakly coordinating Lewis acids such as $B(C_6F_5)_3$ are also suitable Lewis acids within the context of the invention.

As one skilled in the art will recognize the aforementioned listing of Lewis acids is not exhaustive and is provided for illustration. For a more information regarding Lewis acids in polymerization processes, see, for example, International Application Nos. PCT/US03/40903 and PCT/US03/40340.

Initiator

Initiators useful in this invention are those initiators which are capable of being complexed in a suitable diluent with the chosen Lewis acid to yield a complex which rapidly reacts with the olefin thereby forming a propagating polymer chain. Illustrative examples include Brønsted acids such as $H_2O$, HCl, RCOOH (wherein R is an alkyl group), and alkyl halides, such as $(CH_3)_3CCl$, $C_6H_5C(CH_3)_2Cl$ and (2-Chloro-2,4,4-trimethylpentane). More recently, transition metal complexes, such as metallocenes and other such materials that can act as single site catalyst systems, such as when activated with weakly coordinating Lewis acids or Lewis acid salts have been used to initiate isobutylene polymerization.

In an embodiment, the initiator comprises one or more of a hydrogen halide, a carboxylic acid, a carboxylic acid halide, a sulfonic acid, an alcohol, a phenol, a tertiary alkyl halide, a tertiary aralkyl halide, a tertiary alkyl ester, a tertiary aralkyl ester, a tertiary alkyl ether, a tertiary aralkyl ether, alkyl halide, aryl halide, alkylaryl halide, or arylalkylacid halide.

As one skilled in the art will recognize the aforementioned listing of initiator(s) is not exhaustive and is provided for illustration. For a more information regarding initiator(s) in polymerization processes, see, for example, International Application Nos. PCT/US03/40903 and PCT/US03/40340.

Hydrofluorocarbons

Hydrofluorocarbons are preferably used as diluents in the present invention, alone or in combination with other hydrofluorocarbons or in combination with other diluents. For purposes of this invention and the claims thereto, hydrofluorocarbons ("HFC's" or "HFC") are defined to be saturated or unsaturated compounds consisting essentially of hydrogen, carbon and fluorine, provided that at least one carbon, at least one hydrogen and at least one fluorine are present.

In certain embodiments, the diluent comprises hydrofluorocarbons represented by the formula: $C_xH_yF_z$ wherein x is an integer from 1 to 40, alternatively from 1 to 30, alternatively from 1 to 20, alternatively from 1 to 10, alternatively from 1 to 6, alternatively from 2 to 20 alternatively from 3 to 10, alternatively from 3 to 6, most preferably from 1 to 3, wherein y and z are integers and at least one.

Illustrative examples include fluoromethane; difluoromethane; trifluoromethane; fluoroethane; 1,1-difluoroethane; 1,2-difluoroethane; 1,1,1-trifluoroethane; 1,1,2-trifluoroethane; 1,1,1,2-tetrafluoroethane; 1,1,2,2-tetrafluoroethane; 1,1,1,2,2-pentafluoroethane; 1-fluoropropane; 2-fluoropropane; 1,1-difluoropropane; 1,2-difluoropropane; 1,3-difluoropropane; 2,2-difluoropropane; 1,1,1-trifluoropropane; 1,1,2-trifluoropropane; 1,1,3-trifluoropropane; 1,2,2-trifluoropropane; 1,2,3-trifluoropropane; 1,1,1,2-tetrafluoropropane; 1,1,1,3-tetrafluoropropane; 1,1,2,2-tetrafluoropropane; 1,1,2,3-tetrafluoropropane; 1,1,3,3-tetrafluoropropane; 1,2,2,3-tetrafluoropropane; 1,1,1,2,2-pentafluoropropane; 1,1,1,2,3-pentafluoropropane; 1,1,1,3,3-pentafluoropropane; 1,1,2,2,3-pentafluoropropane; 1,1,2,3,3-pentafluoropropane; 1,1,1,2,2,3-hexafluoropropane; 1,1,1,2,3,3-hexafluoropropane; 1,1,1,3,3,3-hexafluoropropane; 1,1,2,2,3,3-hexafluoropropane; 1,1,1,2,2,3,3-heptafluoropropane; 1,1,1,2,3,3,3-heptafluoropropane; 1-fluorobutane; 2-fluorobutane; 1,1-difluorobutane; 1,2-difluorobutane; 1,3-difluorobutane; 1,4-difluorobutane; 2,2-difluorobutane; 2,3-difluorobutane; 1,1,1-trifluorobutane; 1,1,2-trifluorobutane; 1,1,3-trifluorobutane; 1,1,4-trifluorobutane; 1,2,2-trifluorobutane; 1,2,3-trifluorobutane; 1,3,3-trifluorobutane; 2,2,3-trifluorobutane; 1,1,1,2-tetrafluorobutane; 1,1,1,3-tetrafluorobutane; 1,1,1,4-tetrafluorobutane; 1,1,2,2-tetrafluorobutane; 1,1,2,3-tetrafluorobutane; 1,1,2,4-tetrafluorobutane; 1,1,3,3-tetrafluorobutane; 1,1,3,4-tetrafluorobutane; 1,1,4,4-tetrafluorobutane; 1,2,2,3-tetrafluorobutane; 1,2,2,4-tetrafluorobutane; 1,2,3,3-tetrafluorobutane; 1,2,3,4-tetrafluorobutane; 2,2,3,3-tetrafluorobutane; 1,1,1,2,2-pentafluorobutane; 1,1,1,2,3-pentafluorobutane; 1,1,1,2,4-pentafluorobutane; 1,1,1,3,3-pentafluorobutane; 1,1,1,3,4-pentafluorobutane; 1,1,1,4,4-pentafluorobutane; 1,1,2,2,3-pentafluorobutane; 1,1,2,2,4-pentafluorobutane; 1,1,2,3,3-pentafluorobutane; 1,1,2,4,4-pentafluorobutane; 1,1,3,3,4-pentafluorobutane; 1,2,2,3,3-pentafluorobutane; 1,2,2,3,4-pentafluorobutane; 1,1,1,2,2,3-hexafluorobutane; 1,1,1,2,2,4-hexafluorobutane; 1,1,1,2,3,3- hexafluorobutane, 1,1,1,2,3,4-hexafluorobutane; 1,1,1,2,4,4-hexafluorobutane; 1,1,1,3,3,4-hexafluorobutane; 1,1,1,3,4,4-hexafluorobutane; 1,1,1,4,4,4-hexafluorobutane; 1,1,2,2,3,3-hexafluorobutane; 1,1,2,2,3,4-hexafluorobutane; 1,1,2,2,4,4-hexafluorobutane; 1,1,2,3,3,4-hexafluorobutane; 1,1,2,3,4,4-hexafluorobutane; 1,2,2,3,3,4-hexafluorobutane; 1,1,1,2,2,3,3-heptafluorobutane; 1,1,1,2,2,4,4-heptafluorobutane; 1,1,1,2,2,3,4-heptafluorobutane; 1,1,1,2,3,3,4-heptafluorobutane; 1,1,1,2,3,4,4-heptafluorobutane; 1,1,1,2,4,4,4-heptafluorobutane; 1,1,1,3,3,4,4-heptafluorobutane; 1,1,1,2,2,3,3,4-octafluorobutane; 1,1,1,2,2,3,4,4-octafluorobutane; 1,1,1,2,3,3,4,4-octafluorobutane; 1,1,1,2,2,4,4,4-octafluorobutane; 1,1,1,2,3,4,4,4-octafluorobutane; 1,1,1,2,2,3,3,4,4-nonafluorobutane; 1,1,1,2,2,3,4,4,4-nonafluorobutane; 1-fluoro-2-methylpropane; 1,1-difluoro-2-methylpropane; 1,3-difluoro-2-methylpropane; 1,1,1-trifluoro-2-methylpropane; 1,1,3-trifluoro-2-methylpropane; 1,3-difluoro-2-(fluoromethyl)propane; 1,1,1,3-tetrafluoro-2-methylpropane; 1,1,3,3-tetrafluoro-2-methylpropane; 1,1,3-trifluoro-2-(fluoromethyl)propane; 1,1,1,3,3-pentafluoro-2-methylpropane; 1,1,3,3-tetrafluoro-2-(fluoromethyl)propane; 1,1,1,3-tetrafluoro-2-(fluoromethyl)propane; fluorocyclobutane; 1,1-difluorocyclobutane; 1,2-difluorocyclobutane; 1,3-difluorocyclobutane; 1,1,2-trifluorocyclobutane; 1,1,3-trifluorocyclobutane; 1,2,3-trifluorocyclobutane; 1,1,2,2-tetrafluorocyclobutane; 1,1,3,3-tetrafluorocyclobutane; 1,1,2,2,3-pentafluorocyclobutane; 1,1,2,3,3-pentafluorocyclobutane; 1,1,2,2,3,3-hexafluorocyclobutane; 1,1,2,2,3,4-hexafluorocyclobutane; 1,1,2,3,3,4-hexafluorocyclobutane; 1,1,2,2,3,3,4-heptafluorocyclobutane; and mixtures thereof and including mixtures of unsaturated HFC's described below. Particularly preferred HFC's include difluoromethane, trifluoromethane, 1,1-difluoroethane, 1,1,1-trifluoroethane, fluoromethane, and 1,1,1,2-tetrafluoroethane.

Illustrative examples of unsaturated hydrofluorocarbons include vinyl fluoride; 1,1-difluoroethene; 1,2-difluoroethene; 1,1,2-trifluoroethene; 1-fluoropropene, 1,1-difluoropropene; 1,2-difluoropropene; 1,3-difluoropropene; 2,3-difluoropropene; 3,3-difluoropropene; 1,1,2-trifluoropropene; 1,1,3-trifluoropropene; 1,2,3-trifluoropropene; 1,3,3-trifluoropropene; 2,3,3-trifluoropropene; 3,3,3-trifluoropropene; 1-fluoro-1-butene; 2-fluoro-1-butene; 3-fluoro-1-butene; 4-fluoro-1-butene; 1,1-difluoro-1-butene; 1,2-difluoro-1-butene; 1,3-difluoropropene; 1,4-difluoro-1-butene; 2,3-difluoro-1-butene; 2,4-difluoro-1-butene; 3,3-difluoro-1-butene; 3,4-difluoro-1-butene; 4,4-difluoro-1-butene; 1,1,2-trifluoro-1-butene; 1,1,3-trifluoro-1-butene; 1,1,4-trifluoro-1-butene; 1,2,3-trifluoro-1-butene; 1,2,4-trifluoro-1-butene; 1,3,3-trifluoro-1-butene; 1,3,4-trifluoro-1-butene; 1,4,4-trifluoro-1-butene; 2,3,3-trifluoro-1-butene; 2,3,4-trifluoro-1-butene; 2,4,4-trifluoro-1-butene; 3,3,4-trifluoro-1-butene; 3,4,4-trifluoro-1-butene; 4,4,4-trifluoro-1-butene; 1,1,2,3-tetrafluoro-1-butene; 1,1,2,4-tetrafluoro-1-butene; 1,1,3,3-tetrafluoro-1-butene; 1,1,3,4-tetrafluoro-1-butene; 1,1,4,4-tetrafluoro-1-butene; 1,2,3,3-tetrafluoro-1-butene; 1,2,3,4-tetrafluoro-1-butene; 1,2,4,4-tetrafluoro-1-butene; 1,3,3,4-tetrafluoro-1-butene; 1,3,4,4-tetrafluoro-1-butene; 1,4,4,4-tetrafluoro-1-butene; 2,3,3,4-tetrafluoro-1-butene; 2,3,4,4-tetrafluoro-1-butene; 2,4,4,4-tetrafluoro-1-butene; 3,3,4,4-tetrafluoro-1-butene; 3,4,4,4-tetrafluoro-1-butene; 1,1,2,3,3-pentafluoro-1-butene; 1,1,2,3,4-pentafluoro-1-butene; 1,1,2,4,4-pentafluoro-1-butene; 1,1,3,3,4-pentafluoro-1-butene; 1,1,3,4,4-pentafluoro-1-butene; 1,1,4,4,4-pentafluoro-1-butene; 1,2,3,3,4-pentafluoro-1-butene; 1,2,3,4,4-pentafluoro-1-butene; 1,2,4,4,4-pentafluoro-1-butene; 2,3,3,4,4-pentafluoro-1-butene; 2,3,4,4,4-pentafluoro-1-butene; 3,3,4,4,4-pentafluoro-1-butene; 1,1,2,3,3,4-hexafluoro-1-butene; 1,1,2,3,4,4-hexafluoro-1-butene; 1,1,2,4,4,4-hexafluoro-1-butene; 1,2,3,3,4,4-hexafluoro-1-butene; 1,2,3,4,4,4-hexafluoro-1-butene; 2,3,3,4,4,4-hexafluoro-1-butene; 1,1,2,3,3,4,4-heptafluoro-1-butene; 1,1,2,3,4,4,4-heptafluoro-1-butene; 1,1,3,3,4,4,4-heptafluoro-1-butene; 1,2,3,3,4,4,4-heptafluoro-1-butene; 1-fluoro-2-butene; 2-fluoro-2-butene; 1,1-difluoro-2-butene; 1,2-difluoro-2-butene; 1,3-difluoro-2-butene; 1,4-difluoro-2-butene; 2,3-difluoro-2-butene; 1,1,1-trifluoro-2-butene; 1,1,2-trifluoro-2-butene; 1,1,3-trifluoro-2-butene; 1,1,4-trifluoro-2-butene; 1,2,3-trifluoro-2-butene; 1,2,4-trifluoro-2-butene; 1,1,1,2-tetrafluoro-2-butene; 1,1,1,3-tetrafluoro-2-butene; 1,1,1,4-tetrafluoro-2-butene; 1,1,2,3-tetrafluoro-2-butene; 1,1,2,4-tetrafluoro-2-butene; 1,2,3,4-tetrafluoro-2-butene; 1,1,1,2,3-pentafluoro-2-butene; 1,1,1,2,4-pentafluoro-2-butene; 1,1,1,3,4-pentafluoro-2-butene; 1,1,1,4,4-pentafluoro-2-butene; 1,1,2,3,4-pentafluoro-2-butene; 1,1,2,4,4-pentafluoro-2-butene; 1,1,1,2,3,4-hexafluoro-2-butene; 1,1,1,2,4,4-hexafluoro-2-butene; 1,1,1,3,4,4-hexafluoro-2-butene; 1,1,1,4,4,4-hexafluoro-2-butene; 1,1,2,3,4,4-hexafluoro-2-butene; 1,1,1,2,3,4,4-heptafluoro-2-butene; 1,1,1,2,4,4,4-heptafluoro-2-butene; and mixtures thereof and including mixtures of saturated HFC's described above.

In one embodiment, the diluent comprises non-perfluorinated compounds or the diluent is a non-perfluorinated diluent. Perfluorinated compounds being those compounds consisting of carbon and fluorine. However, in another embodiment, when the diluent comprises a blend, the blend may comprise perfluorinated compound, preferably, the catalyst, monomer, and diluent are present in a single phase or the aforementioned components are miscible with the diluent as described in further detail below. In another embodiment, the blend may also comprise chlorofluorocarbons (CFC's), or those compounds consisting of chlorine, fluorine, and carbon.

In another embodiment, when higher weight average molecular weights (Mw) (typically greater than 10,000 Mw, preferably more than 50,000 Mw, more preferably more than 100,000 Mw) are desired, suitable diluents include hydrofluorocarbons with a dielectric constant of greater than 10 at −85° C., preferably greater than 15, more preferably greater than 20, more preferably greater than 25, more preferably 40 or more. In embodiments where lower molecular weights (typically lower than 10,000 Mw, preferably less than 5,000 Mw, more preferably less than 3,000 Mw) are desired the dielectric constant may be less than 10, or by adding larger amounts of initiator or transfer agent when the dielectric constant is above 10. The dielectric constant of the diluent $\in_D$ is determined from measurements of the capacitance of a parallel-plate capacitor immersed in the diluent [measured value $C_D$], in a reference fluid of known dielectric constant $\in_R$ [measured value $C_R$], and in air ($\in_A=1$) [measured value $C_A$]. In each case the measured capacitance $C_M$ is given by $C_M = \in C_C + C_S$, where $\in$ is the dielectric constant of the fluid in which the capacitor is immersed, $C_C$ is the cell capacitance, and $C_S$ is the stray capacitance. From these measurements $\in_D$ is given by the formula $\in_D = ((C_D - C_A) \in_R + (C_R - C_D))/(C_R - C_A)$. Alternatively, a purpose-built instrument such as the Brookhaven Instrument Corporation BIC-870 may be used to measure dielectric constant of diluents directly. A comparison of the dielectric constants ($\in$) of a few selected diluents at −85° C. is provided below.

| Diluent | ε at −85° C. |
|---|---|
| Methyl chloride | 18.34 |
| Difluoromethane | 36.29 |
| 1,1-difluoroethane | 29.33 |
| 1,1,1-trifluoroethane | 22.18 |
| 1,1,1,2-tetrafluoroethane | 23.25 |
| 1,1,2,2-tetrafluoroethane | 11.27 |
| 1,1,1,2,2-pentafluoroethane | 11.83 |

In other embodiments, one or more HFC's are used in combination with another diluent or mixtures of diluents. Suitable additional diluents include hydrocarbons, especially hexanes and heptanes, halogenated hydrocarbons, especially chlorinated hydrocarbons and the like. Specific examples include but are not limited to propane, isobutane, pentane, methycyclopentane, isohexane, 2-methylpentane, 3-methylpentane, 2-methylbutane, 2,2-dimethylbutane, 2,3-dimethylbutane, 2-methylhexane, 3-methylhexane, 3-ethylpentane, 2,2-dimethylpentane, 2,3-dimethylpentane, 2,4-dimethylpentane, 3,3-dimethyl pentane, 2-methylheptane, 3-ethylhexane, 2,5-dimethylhexane, 2,24, -trimethylpentane, octane, heptane, butane, ethane, methane, nonane, decane, dodecane, undecane, hexane, methyl cyclohexane, cyclopropane, cyclobutane, cyclopentane, methylcyclopentane, 1,1-dimethylcycopentane, cis 1,2-dimethylcyclopentane, trans-1,2-dimethylcyclopentane, trans-1,3-dimethylcyclopentane, ethylcyclopentane, cyclohexane, methylcyclohexane, benzene, toluene, xylene, ortho-xylene, para-xylene, meta-xylene, and the halogenated versions of all of the above, preferably the chlorinated versions of the above, more preferably fluorinated versions of all of the above. Brominated versions of the above are also useful. Specific examples include, methyl chloride, methylene chloride, ethyl chloride, propyl chloride, butyl chloride, chloroform and the like.

In another embodiment, non-reactive olefins may be used as diluents in combination with HFC's. Examples include, but are not limited to, ethylene, propylene, and the like.

In one embodiment, the HFC is used in combination with a chlorinated hydrocarbon such as methyl chloride. Additional embodiments include using the HFC in combination with hexanes or methyl chloride and hexanes. In another embodiment the HFC's are used in combination with one or more gases inert to the polymerization such as carbon dioxide, nitrogen, hydrogen, argon, neon, helium, krypton, zenon, and/or other inert gases that are preferably liquid at entry to the reactor. Preferred gases include carbon dioxide and/or nitrogen.

In another embodiment the HFC's are used in combination with one or more nitrated alkanes, including $C_1$ to $C_{40}$ nitrated linear, cyclic or branched alkanes. Preferred nitrated alkanes include, but are not limited to, nitromethane, nitroethane, nitropropane, nitrobutane, nitropentane, nitrohexane, nitroheptane, nitrooctane, nitrodecane, nitrononane, nitrododecane, nitroundecane, nitrocyclomethane, nitrocycloethane, nitrocyclopropane, nitrocyclobutane, nitrocyclopentane, nitrocyclohexane, nitrocycloheptane, nitrocyclooctane, nitrocyclodecane, nitrocyclononane, nitrocyclododecane, nitrocycloundecane, nitrobenzene, and the di- and tri-nitro versions of the above. A preferred embodiment is HFC's blended with nitromethane.

The HFC is typically present at 1 to 100 volume % based upon the total volume of the diluents, alternatively between 5 and 100 volume %, alternatively between 10 and 100 volume %, alternatively between 15 and 100 volume %, alternatively between 20 and 100 volume %, alternatively between 25 and 100 volume %, alternatively between 30 and 100 volume %, alternatively between 35 and 100 volume %, alternatively between 40 and 100 volume %, alternatively between 45 and 100 volume %, alternatively between 50 and 100 volume %, alternatively between 55 and 100 volume %, alternatively between 60 and 100 volume %, alternatively between 65 and 100 volume %, alternatively between 70 and 100 volume %, alternatively between 75 and 100 volume %, alternatively between 80 and 100 volume %, alternatively between 85 and 100 volume %, alternatively between 90 and 100 volume %, alternatively between 95 and 100 volume %, alternatively between 97 and 100 volume %, alternatively between 98 and 100 volume %, and alternatively between 99 and 100 volume %. In a preferred embodiment the HFC is blended with one or more chlorinated hydrocarbons. In another preferred embodiment the HFC is selected from the group consisting of difluoromethane, trifluoromethane, 1,1-difluoroethane, 1,1,1-trifluoroethane, and 1,1,1,2-tetrafluoroethane and mixtures thereof.

In another embodiment the diluent or diluent mixture is selected based upon its solubility in the polymer. Certain diluents are soluble in the polymer. Preferred diluents have little to no solubility in the polymer. Solubility in the polymer is measured by forming the polymer into a film of thickness between 50 and 100 microns, then soaking it in diluent (enough to cover the film) for 4 hours at −75° C. The film is removed from the diluent, exposed to room temperature for 90 seconds to evaporate excess diluent from the surface of the film, and weighed. The mass uptake is defined as the percentage increase in the film weight after soaking. The diluent or diluent mixture is chosen so that the polymer has a mass uptake of less than 4 wt %, preferably less than 3 wt %, preferably less than 2 wt %, preferably less than 1 wt %, more preferably less than 0.5 wt %.

In a preferred embodiment, the diluent or diluent mixture is selected such that the difference between the measured glass transition temperature Tg of the polymer with less than 0.1 wt % of any diluent, unreacted monomers and additives is within 15° C. of the Tg of the polymer measured after it has been formed into a film of thickness between 50 and 100 microns, that has been soaked in diluent (enough to cover the film) for 4 hours at −75° C. The glass transition temperature is determined by differential scanning calorimetry (DSC). Techniques are well described in the literature, for example, B. Wunderlich, "The Nature of the Glass Transition and its Determination by Thermal Analysis", in *Assignment of the Glass Transition*, ASTM STP 1249, R. J. Seyler, Ed., American Society for Testing and Materials, Philadelphia, 1994, pp. 17-31. The sample is prepared as described above, sealed immediately after soaking into a DSC sample pan, and maintained at a temperature below −80° C. until immediately before the DSC measurement. Preferably the Tg values are within 12° C. of each other, preferably within 11° C. of each other, preferably within 10° C. of each other, preferably within 9° C. of each other, preferably within 8° C. of each other, preferably within 7° C. of each other, preferably within 6° C. of each other, preferably within 5° C. of each other, preferably within 4° C. of each other, preferably within 3° C. of each other, preferably within 3° C. of each other, preferably within 2° C. of each other, preferably within 1° C. of each other.

Polymerization Process

The invention may be practiced in continuous and batch processes. Further the invention may be practiced in a plug flow reactor and/or stirred tank reactors. In particular this invention may be practiced in "butyl reactors." Illustrative examples include any reactor selected from the group consisting of a continuous flow stirred tank reactor, a plug flow reactor, a moving belt or drum reactor, a jet or nozzle reactor, a tubular reactor, and an autorefrigerated boiling-pool reactor.

In certain embodiments, the invention is practiced using a slurry polymerization process. The polymerization processes of the invention may be a cationic polymerization process. The polymerization process of the invention may be a continuous polymerization process. The polymerization processes of the invention may be a polymerization processes for the production of $C_4$-$C_7$ isoolefin polymers such as isobutylene based polymers.

In one embodiment, the polymerization is carried out where the catalyst, monomer, and diluent are present in a single phase. Preferably, the polymerization is carried-out in a continuous polymerization process in which the catalyst, monomer(s), and diluent are present as a single phase. In slurry polymerization, the monomers, catalyst(s), and initiator(s) are all miscible in the diluent or diluent mixture, i.e., constitute a single phase, while the polymer precipitates from the diluent with good separation from the diluent. Desirably, reduced or no polymer "swelling" is exhibited as indicated by little or no Tg suppression of the polymer and/or little or no diluent mass uptake. Thus, polymerization in the diluents of the present invention provides for high polymer concentration to be handled at low viscosity with good heat transfer, reduced reactor fouling, homogeneous polymerization and/or the convenience of subsequent reactions to be run directly on the resulting polymer mixture.

The reacted monomers within the reactor form part of a slurry. In one embodiment, the concentration of the solids in the slurry is equal to or greater than 10 vol %. In another embodiment, the concentration of solids in the slurry is present in the reactor equal to or greater than 25 vol %. In yet another embodiment, the concentration of solids in the slurry is less than or equal to 75 vol %. In yet another embodiment, the concentration of solids in slurry is present in the reactor from 1 to 70 vol %. In yet another embodiment, the concentration of solids in slurry is present in the reactor from 5 to 70 vol %. In yet another embodiment, the concentration of solids in slurry concentration is present in the reactor from 10 to 70 vol %. In yet another embodiment, the concentration of solids in slurry concentration is present in the reactor from 15 to 70 vol %. In yet another embodiment, the concentration of solids in slurry concentration is present in the reactor from 20 to 70 vol %. In yet another embodiment, the concentration of solids in slurry concentration is present in the reactor from 25 to 70 vol %. In yet another embodiment, the concentration of solids in slurry concentration is present in the reactor from 30 to 70 vol %. In yet another embodiment, the concentration of solids in slurry concentration is present in the reactor from 40 to 70 vol %.

The order of contacting the monomer feed-stream, catalyst, initiator, and diluent may vary from one embodiment to another.

For a more information regarding polymerization processes, see, for example, International Application Nos. PCT/US03/40903 and PCT/US03/40340.

Extractive Distillation

To recover unreacted monomers such as isobutylene and mixture components such as diluent components such as HFCs for recycle to the polymerization process, extractive distillation is employed. In so doing, diluent components such as HFCs may be recycled as a carrier for the catalyst system or catalyst components being free of monomers or essentially free of monomers such as isobutylene and other monomers/comonomers.

In certain embodiments, essentially free of monomers refers to low part per million levels of monomers by weight. In particular, for an HFC/monomer mixture, an extractive distillation system using a suitable hydrocarbon as the extractive agent can provide a clean HFC stream where monomer levels from less than 100 wppm can be achieved, alternatively, from less than 30 wppm, alternatively, from less than 5 wppm, and alternatively, less than 2 wppm. If enough trays are provided in the extraction column, no traceable monomer is left in the HFC distillate.

For example, for the R134a/isobutylene mixture, an extractive distillation system using n-hexane as the extractive agent can provide a clean R134a stream where isobutylene levels from less than 100 wppm can be achieved, alternatively, from less than 30 wppm, alternatively, from less than 5 wppm, and alternatively, less than 2 wppm. If enough trays are provided in the extraction column, essentially no isobutylene monomer is left in the R134a distillate.

Extractive distillation is a technique well-known in the art. It generally refers to a distillative separation of at least two components facilitated by increasing the relative volatility of the two components by adding a third component. For example, the process may be generally carried-out in a continuous distillation column, comprising a multi-stage distillation column with a minimum of two feed points, a reboiler, and an overhead condenser for returning reflux to the column. For more information, see, e.g., U.S. Pat. Nos. 5,087,329, 5,200,431, 5,470,442, 5,723,429, 5,744,662, 5,830,325, 6,156,161, 6,307,115, 6,527,917, and EP 1 003 699 B.

Figure 1:
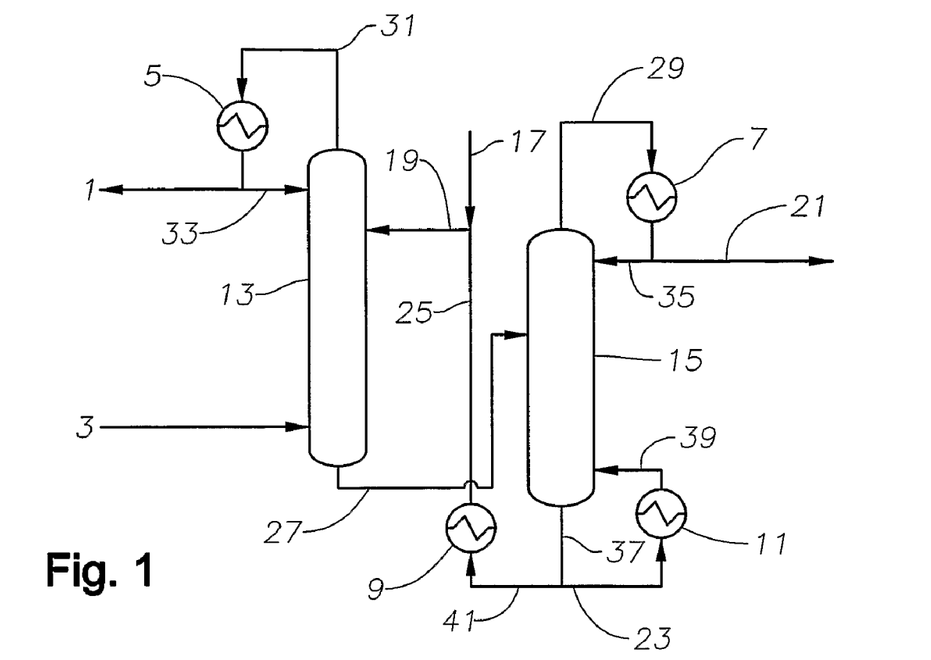
FIG. 1 represents an embodiment of an extractive distillation system.

In an embodiment, extractive distillation occurs in accordance with the extractive distillation system depicted in FIG. 1. A vapor feed stream 3 containing a hydrofluorocarbon and a monomer is admitted to the bottom section of a first column 13. A liquid extraction agent 19 is admitted to a section of the column 13 several trays below the top of the column. The trays above the point where the extraction agent 19 is admitted serve to fractionate or separate the extraction agent from the hydrofluorocarbon in the overhead distillate 1. The trays below the point where the extraction agent 19 is admitted serve to extract the monomers from the feed 3 mixture of hydrofluorocarbon and monomer(s). The overhead vapor 31 from column 13 is condensed in exchanger 5, and a portion of the condensate is returned to the top tray of column 13 as reflux 33. The remaining condensate 1 from the condensing exchanger 5 is withdrawn and is a hydrofluorocarbon stream that is essentially free of any monomers and is sent to the catalyst blending section. The bottoms liquid 27 from column 13 contains a mixture of extraction agent, hydrofluorocarbon and monomers and it is sent to a point approximately at the middle of a second column 15. The trays above the column 15 feed point 27 serve to fractionate or separate the extraction agent from the hydrofluorocarbons and monomer(s). The trays below the column 15 feed point 27 serve to fractionate or separate essentially all of the monomers from the extraction agent. The overhead vapor 29 from column 15 is condensed in exchanger 7 and a portion of the condensate is returned to the top tray of column 15 as reflux 35. The remaining condensate 21 from the condensing exchanger 7 is withdrawn and is a mixture of hydrofluorocarbon and monomer(s) and is sent to the reactor feed blending section. A portion 23 of the bottoms liquid 37 from column 15 is sent to a vaporizing exchanger 11 and a vapor or liquid/vapor mixture 39 is returned to the bottom tray of the column. The column 15 bottoms stream 37 is the extraction agent that is essentially free of monomers. The remaining portion 41 of the bottoms liquid 37 from column 15 is sent to a cooling exchanger 9, and the cooled stream 25 is premixed with makeup extraction agent 17 to account for minor losses in the process.

Figure 2:
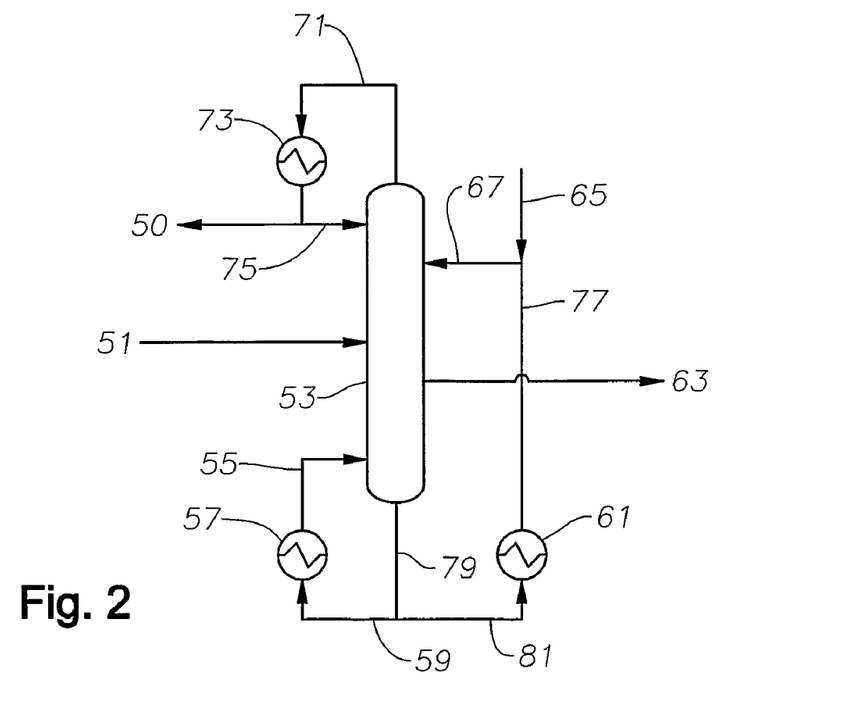
FIG. 2 represents another embodiment of an extractive distillation system.

In another embodiment, extractive distillation occurs in accordance with the extractive distillation system depicted in FIG. 2. A vapor feed stream 51 containing a hydrofluorocarbon and a monomer is admitted to the middle section of a column 53. A liquid extraction agent 67 is admitted to a section of the column 53 several trays below the top of the column. The trays above the point where the extraction agent 67 is admitted serve to fractionate or separate the extraction agent from the hydrofluorocarbon in the overhead distillate 50. The trays below the point where the extraction agent 67 is admitted and above the point where the feed 51 is admitted serve to extract the monomers from the feed 51 mixture of hydrofluorocarbon and monomer(s). The overhead vapor 71 from column 53 is condensed in exchanger 73, and a portion of the condensate is returned to the top tray of column 53 as reflux 75. The remaining condensate 50 from the condensing exchanger 73 is withdrawn and is a hydrofluorocarbon stream that is essentially free of any monomers and is sent to the catalyst blending section. A sidestream vapor 63 from column 53 contains a mixture of hydrofluorocarbon, essentially all of the monomers that are admitted via feed stream 51, and a minor amount of extraction agent, Vapor sidestream 63 is sent back to the reactor section where it combines with the reactor effluent stream. The trays below the column 53 feed point 51 and above the sidestream vapor drawoff 63 serve to improve the recovery of hydrofluorocarbon in the overhead distillate 50 and minimize the recycle of hydrofluorocarbon in stream 63 to the reactor section. The trays below the sidestream vapor drawoff 63 serve to fractionate or separate essentially all of the monomers from the extraction agent. A portion 59 of the bottoms liquid 79 from column 53 is sent to a vaporizing exchanger 57 and a vapor or liquid/vapor mixture 55 is returned to the bottom tray of the column. The column 53 bottoms stream 79 is the extraction agent that is essentially free of monomers. The remaining portion 81 of the bottoms liquid 79 from column 53 is sent to a cooling exchanger 61, and the cooled stream 77 is premixed with makeup extraction agent 65 to account for minor losses in the process.

One skilled in the art will recognize all ancillary equipment such as mechanisms for chemical transport such as pumps and optional equipment that may be combined with the aforementioned embodiments.

Additionally, one skilled in the art will also recognize alternatives to the use of trays in the aforementioned columns such as packing materials including loose packings such as pall rings, rashing rings, and the like as well as structured packings.

Extractive agent refers to a higher boiling solvent that is added to the azeotropic mixture or azeotrope-like mixture to alter the relative volatilities of the components. The choice of extractive agent is made to avoid the formation of additional azeotropes or the like and allows separation of the components of the original constant boiling mixture. In embodiment, the extractive agent refers to any material that can separate diluent components from at least one monomer.

In an embodiment, the extractive agent comprises or consists essentially of a hydrocarbon.

In an embodiment, the extractive agent comprises hydrocarbons such as hexane and heptane.

In other embodiments, examples include but are not limited to butane, pentane, methycyclopentane, isohexane, 2-methylpentane, 3-methylpentane, 2-methylbutane, 2,2-dimethylbutane, 2,3-dimethylbutane, 2-methylhexane, 3-methylhexane, 3-ethylpentane, 2,2-dimethylpentane, 2,3-dimethylpentane, 2,4-dimethylpentane, 3,3-dimethyl pentane, 2-methylheptane, 3-ethylhexane, 2,5-dimethylhexane, 2,24, -trimethylpentane, octane, heptane, butane, nonane, decane, dodecane, undecane, hexane, methyl cyclohexane, cyclopropane, cyclobutane, cyclopentane, methylcyclopentane, 1,1-dimethylcyclopentane, cis 1,2-dimethylcyclopentane, trans-1,2-dimethylcyclopentane, trans-1,3-dimethylcyclopentane, ethylcyclopentane, cyclohexane, methylcyclohexane, benzene, toluene, xylene, ortho-xylene, para-xylene, meta-xylene, and mixtures thereof.

In another embodiment, the extractive agent comprises hydrocarbons such as alkanes, including $C_4$ to $C_{22}$ linear, cyclic, branched alkanes, alkenes, aromatics, and mixtures thereof. Examples include butane, pentane, methycyclopentane, isohexane, 2-methylpentane, 3-methylpentane, 2-methylbutane, 2,2-dimethylbutane, 2,3-dimethylbutane, 2-methylhexane, 3-methylhexane, 3-ethylpentane, 2,2-dimethylpentane, 2,3-dimethylpentane, 2,4-dimethylpentane, 3,3-dimethyl pentane, 2-methylheptane, 3-ethylhexane, 2,5-dimethylhexane, 2,2,4, -trimethylpentane, octane, heptane, butane, nonane, decane, dodecane, undecane, hexane, methyl cyclohexane, cyclopropane, cyclobutane, cyclopentane, methylcyclopentane, 1,1-dimethylcyclopentane, cis 1,2-dimethylcyclopentane, trans-1,2-dimethylcyclopentane, trans-1,3-dimethylcyclopentane, ethylcyclopentane, cyclohexane, methylcyclohexane, and mixtures thereof. Other examples of hydrocarbons include benzene, toluene, xylene, ortho-xylene, para-xylene, meta-xylene.

In certain embodiments, n-hexane and/or mixtures of hexane isomers can be used as an extractive agent in the separation of isobutylene from R134a or R152a. It is believed that the introduction of an effective amount of hexane to the mixture of isobutylene and HFC being fractionated (to recover a portion of HFC) reduces the effective activity coefficient of isobutylene relative to HFC. This reduces the volatility of isobutylene in the presence of HFC during distillation and avoids the azeotrope or azeotropic-like behavior between isobutylene and R134a or R152a.

In these embodiments, n-hexane and/or mixtures of hexane isomers are well-suited in the practice of the invention because they have a high enough boiling point relative to the R134a/isobutylene mixture or R152a/isobutylene mixture to allow separation of the components in the original constant boiling mixture and avoids the formation of new azeotropes between the hexane(s) and R134a/R152a. Additionally, hexanes have a lower molecular weight and lower boiling temperature in the towers compared to saturated or unsaturated hydrocarbons containing more carbon atoms. This leads to more moderate conditions of temperature and pressure in the distillation equipment.

In certain embodiments, saturated hydrocarbons are preferred over unsaturated hydrocarbons due to their lower reactivity toward formation of undesirable byproducts (polymers, oligomers, etc). Extraction agents that are lighter than hexane or the like are less desirable because they have a greater tendency to form azeotropes with the HFC and they require more trays in the distillation tower(s) to make the required separation due to the lower relative volatility versus isobutylene and/or lower relative volatility versus the R134a or R152a.

In certain embodiments, it is desirable that the extraction agent be soluble in the HFC over the range of temperatures that the extraction tower(s) will be operated and that the extraction solvent not form an azeotrope itself with the HFC.

The effective amount of the extractive agent can vary widely. In general, however, using an increased amount of extractive agent will enhance the recovery of the diluent component such as the HFC. For example, the ratio of the extractive agent to the diluent is from about 0.2:1.0 to about 1.0:0.2 on a molar basis, alternatively, from about 0.3:1.0 to about 1.0:0.3, alternatively, from about 0.5:1.0 to about 1.0:0.5, and alternatively, from about 0.7:1.0 to about 1.0:0.7.

In an embodiment, R134a and isobutylene form azeotropic compositions at 0.84 mole fraction R134a at 25° C. and at 0.88 mole fraction R134a at 75° C. R134a and isobutylene also form azeotrope-like mixtures in the range from 0.750 to 0.999 mole fraction R134a at 25° C. and 75° C. Any mixture of R134a and isobutylene can be separated using the extractive distillation process described herein.

Figure 3:
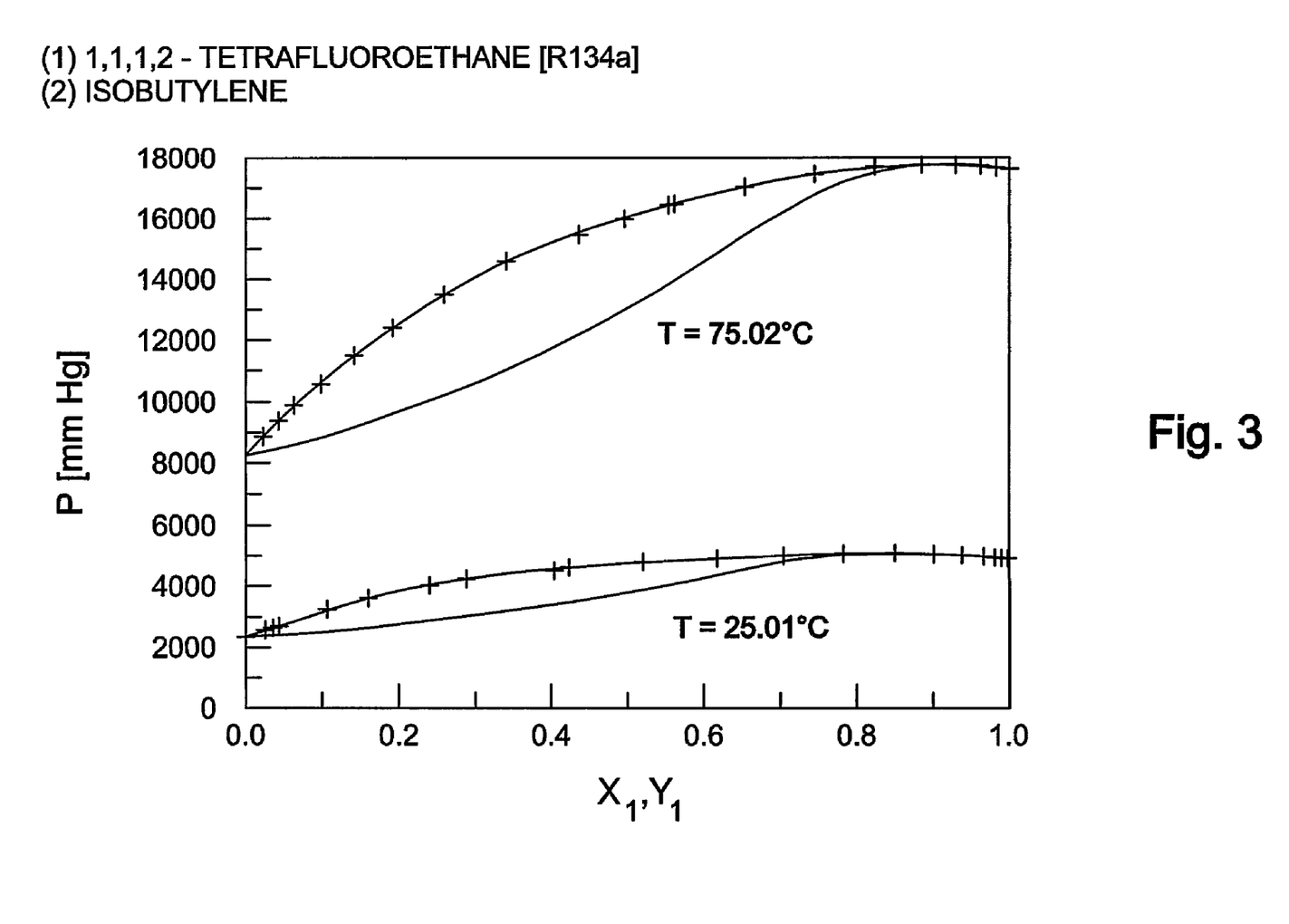

FIG. 3 shows a plot of the vapor pressure of mixtures of 1,1,1,2 tetrafluoroethane (134a) and isobutylene over the entire range of compositions from 0.0 to 1.0 mole fraction R134a. Data is shown for two temperature levels, 25° C. and 75° C. From the plot, it is clear that a maximum vapor pressure is found at the azeotropic composition and that there is a range of compositions from about 0.750 to 0.999 mole fraction R134a where the vapor pressures are essentially constant, indicating azeotrope like compositions over this entire range.

In another embodiment, R152a and isobutylene form azeotropic compositions at 0.87 mole fraction R152a at 25° C. and at 0.94 mole fraction R152a at 75° C. R152a and isobutylene also form azeotrope like mixtures in the range from 0.750 to 0.999 mole fraction R152a at 25° C. and 75° C. Any mixture of R152a and isobutylene can be separated using the extractive distillation process described herein.

Figure 4:
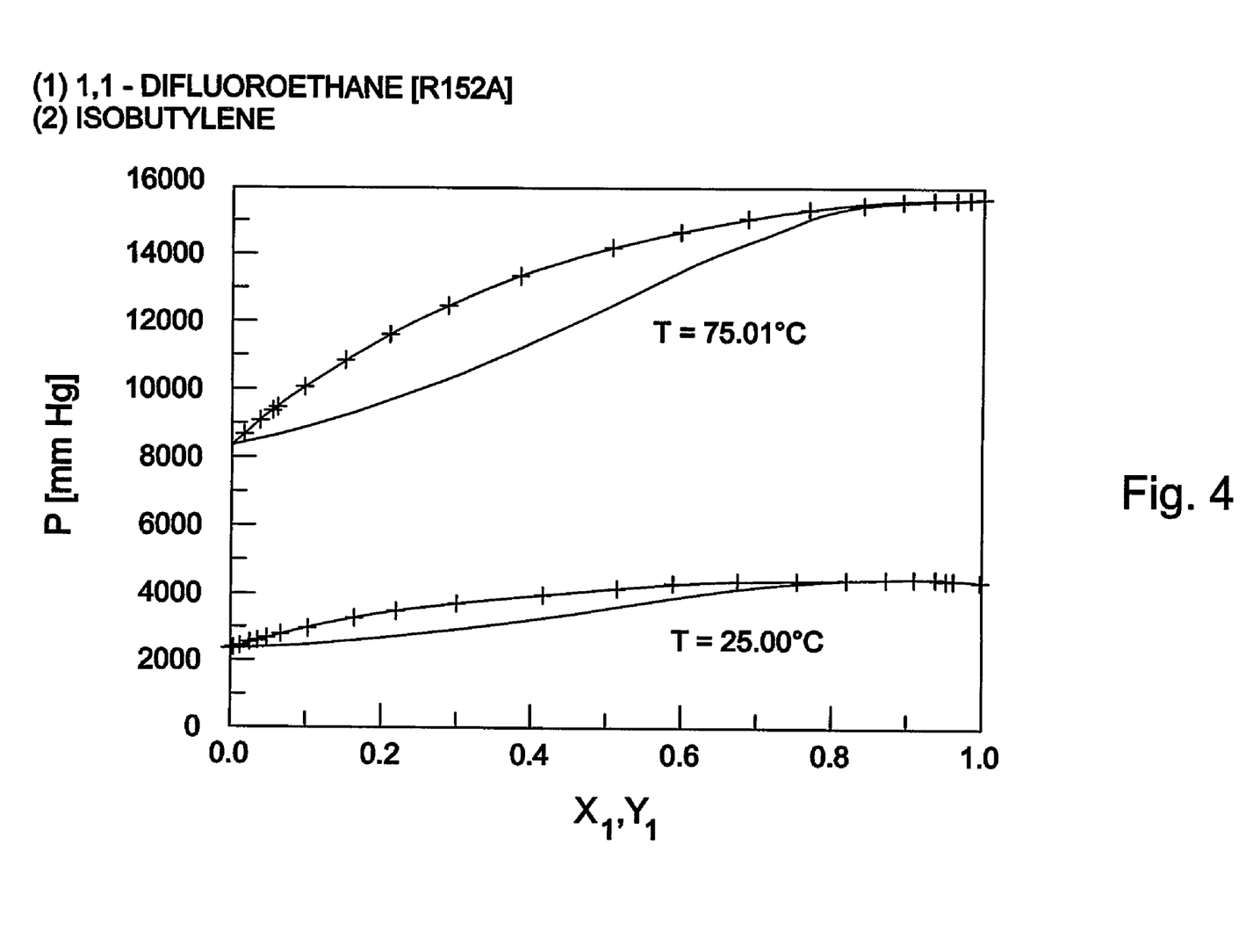

FIG. 4 shows a plot of the vapor pressure of mixtures of 1,1 difluoroethane (152a) and isobutylene over the entire range of compositions from 0 to 1.0 mole fraction R152a. Data is shown for two temperature levels, 25° C. and 75° C. From the plot, it is clear that a maximum vapor pressure is found at the azeotropic composition and that there is a range of compositions from about 0.750 to 0.999 mole fraction R152a where the vapor pressures are essentially constant, indicating azeotrope like compositions over this entire range.

INDUSTRIAL APPLICATIONS

The invention described herein may be used to manufacture polymers useful in wide variety of applications. The low degree of permeability to gases accounts for the largest uses of these polymers, namely inner tubes and tire innerliners. These same properties are also of importance in air cushions, pneumatic springs, air bellows, accumulator bags, and pharmaceutical closures. The thermal stability of the polymers of the invention make them ideal for rubber tire-curing bladders, high temperature service hoses, and conveyor belts for hot material handling.

The polymers exhibit high damping and have uniquely broad damping and shock absorption ranges in both temperature and frequency. They are useful in molded rubber parts and find wide applications in automobile suspension bumpers, auto exhaust hangers, and body mounts.

The polymers of the instant invention are also useful in tire sidewalls and tread compounds. In sidewalls, the polymer characteristics impart good ozone resistance, crack cut growth, and appearance. The polymers of the invention may also be blended. Properly formulated blends with high diene rubbers that exhibit phase co-continuity yield excellent sidewalls. Improvements in wet, snow, and ice skid resistances and in dry traction without compromises in abrasion resistance and rolling resistance for high performance tires can be accomplished by using the polymers of the instant invention.

Blends of the polymers of the invention with thermoplastic resins are used for toughening of these compounds. High-density polyethylene and isotactic polypropylene are often modified with 5 to 30 wt % of polyisobutylene. In certain applications, the instant polymers provide for a highly elastic compound that is processable in thermoplastic molding equipment. The polymers of the instant invention may also be blended with polyamides to produce other industrial applications.

The polymers of the instant invention may also be used as adhesives, caulks, sealants, and glazing compounds. They are also useful as plasticizers in rubber formulations with butyl, SBR, and natural rubber. In linear low density polyethylene (LLDPE) blends, they induce cling to stretch-wrap films. They are also widely employed in lubricants as dispersants and in potting and electrical cable filling materials.

In certain applications, the polymers of the invention make them also useful in chewing-gum, as well as in medical applications such as pharmaceutical stoppers, and the arts for paint rollers.

The following examples reflect embodiments of the invention and are by no means intended to be limiting of the scope of the invention.

EXAMPLES

For the VLE measurements (isothermal P-x data) two different static devices were used as described below. However, any device suitable to demonstrate the following principles may be used. In this procedure, the pressure of different overall compositions is measured at constant temperature. The first apparatus can be operated at temperatures between 200 K and 500 K and pressures up to 20 MPa. This apparatus has to be operated manually. The second apparatus is operated by a computer and can be used at temperatures between 278 K and 420 K and pressures up to 2 MPa.

The thermostatted, purified, and degassed compounds (liquids or liquefied gases) are charged into a VLE cell which is evacuated and placed in a thermostatted oil bath. The pressure inside the cell is monitored with a pressure sensor (model PDCR 4010, Druck: range: 0 to 0.35 and 3.5 MPa for the manual set-up and model TJE-CP-1g, Sensotec: range 0 to 2 MPa for the computer-controlled set-up). The pressure sensors were calibrated with a pressure balance (Model 8000S or 21000, D&H). The temperature is measured with a Pt100 resistance thermometer (model 1560, Hart Scientific in both cases). The total compositions are determined from the known quantities of liquids injected into the equilibrium cell by piston injector pumps (model 2200-801, Ruska) in case of the manual apparatus and stepping motor driven injection pumps in case of the computer-operated apparatus. The liquid phase compositions are obtained by solving mass and volume balance equations which are also taking the vapor-liquid equilibrium into account.

TABLE 1

Experimental Px data for the System R134a (1) + iso-butene (2) at 25.01° C.

| $x_1$ | P/kPa |
|---|---|
| 0.0000 | 306.41 |
| 0.0056 | 315.12 |
| 0.0149 | 328.92 |
| 0.0243 | 342.40 |
| 0.0335 | 354.97 |
| 0.0412 | 365.20 |

TABLE 1-continued

Experimental Px data for the System R134a (1) + iso-butene (2) at 25.01° C.

| $x_1$ | P/kPa |
|---|---|
| 0.1036 | 435.67 |
| 0.1581 | 483.49 |
| 0.2368 | 536.77 |
| 0.2871 | 563.46 |
| 0.4021 | 610.21 |
| 0.4221 | 616.73 |
| 0.5199 | 644.04 |
| 0.6167 | 662.79 |
| 0.7037 | 675.22 |
| 0.7831 | 682.29 |
| 0.8504 | 683.99 |
| 0.9015 | 681.61 |
| 0.9387 | 677.12 |
| 0.9657 | 671.92 |
| 0.9823 | 667.68 |
| 0.9902 | 665.39 |
| 0.9968 | 663.29 |
| 1.0000 | 662.28 |

TABLE 2

Experimental Px data for the system R134a (1) + iso-butene (2) at 75.02° C.

| $x_1$ | P/kPa |
|---|---|
| 0.0000 | 1100.0 |
| 0.0218 | 1179.9 |
| 0.0339 | 1222.8 |
| 0.0427 | 1252.4 |
| 0.0556 | 1294.8 |
| 0.0617 | 1313.7 |
| 0.0960 | 1419.0 |
| 0.1395 | 1538.0 |
| 0.1896 | 1658.6 |
| 0.2576 | 1798.9 |
| 0.3410 | 1947.6 |
| 0.4345 | 2068.1 |
| 0.4957 | 2133.2 |
| 0.5530 | 2192.6 |
| 0.5611 | 2198.3 |
| 0.6542 | 2274.6 |
| 0.7442 | 2334.0 |
| 0.8241 | 2367.5 |
| 0.8851 | 2377.5 |
| 0.9300 | 2374.3 |
| 0.9623 | 2365.2 |
| 0.9812 | 2357.1 |
| 0.9893 | 2352.8 |
| 0.9958 | 2349.5 |
| 1.0000 | 2347.2 |

TABLE 3

Azeotropic conditions derived from the Px data

| Component 1 | Component 2 | T/° C. | $y_{1,az}$ | $P_{az}$/kPa |
|---|---|---|---|---|
| R134a | iso-butene | 25.01 | 0.84 | 684 |
| R134a | iso-butene | 75.02 | 0.88 | 2378 |

TABLE 4

Experimental Px data for the system R152a (1) + iso-butene (2) at 25.00° C.

| $x_1$ | P/kPa |
|---|---|
| 0.0000 | 306.02 |
| 0.0067 | 313.32 |
| 0.0145 | 321.58 |
| 0.0221 | 329.62 |
| 0.0292 | 336.91 |
| 0.0361 | 343.56 |
| 0.0497 | 355.99 |
| 0.0690 | 372.68 |
| 0.1038 | 399.33 |
| 0.1647 | 438.19 |
| 0.2201 | 467.03 |
| 0.2995 | 500.31 |
| 0.4151 | 537.19 |
| 0.5148 | 561.42 |
| 0.5902 | 576.18 |
| 0.6754 | 588.55 |
| 0.7536 | 596.98 |
| 0.8206 | 601.59 |
| 0.8713 | 603.10 |
| 0.9090 | 602.80 |
| 0.9367 | 601.72 |
| 0.9537 | 600.66 |
| 0.9614 | 600.05 |
| 0.9954 | 596.54 |
| 1.0000 | 595.98 |

TABLE 5

Experimental Px data for the system R152a (1) + iso-butene (2) at 75.01° C.

| $x_1$ | P/kPa |
|---|---|
| 0.0000 | 1099.5 |
| 0.0176 | 1149.1 |
| 0.0249 | 1168.5 |
| 0.0396 | 1206.4 |
| 0.0553 | 1246.1 |
| 0.0618 | 1261.1 |
| 0.0980 | 1342.8 |
| 0.1516 | 1450.2 |
| 0.2089 | 1550.0 |
| 0.2864 | 1664.9 |
| 0.3824 | 1782.8 |
| 0.5056 | 1893.9 |
| 0.5965 | 1961.9 |
| 0.6847 | 2014.9 |
| 0.7670 | 2054.0 |
| 0.8383 | 2076.9 |
| 0.8923 | 2086.5 |
| 0.9325 | 2090.6 |
| 0.9619 | 2090.1 |
| 0.9799 | 2088.2 |
| 0.9882 | 2086.3 |
| 0.9952 | 2085.9 |
| 1.0000 | 2085.2 |

TABLE 6

Azeotropic conditions derived from the Px data

| Component 1 | Component 2 | T/° C. | $y_{1,az}$ | $P_{az}$/kPa |
|---|---|---|---|---|
| R152a | iso-butene | 25.00 | 0.87 | 603 |
| R152a | iso-butene | 75.01 | 0.94 | 2091 |

TABLE 7

Analytic VLE data for the system R134a (1) + isobutene (2) + n-hexane (3)

| ID | T/° C. | P/bar | $x_1$ | $x_2$ | $x_3$ | $y_1$ | $y_2$ | $y_3$ |
|---|---|---|---|---|---|---|---|---|
| 1 | 40 | 9.978 | 0.94755 | 0.00474 | 0.04771 | 0.98163 | 0.00552 | 0.01285 |
| 2 | 40 | 9.045 | 0.75567 | 0.00498 | 0.23936 | 0.96590 | 0.00360 | 0.03050 |
| 3 | 60 | 14.489 | 0.75848 | 0.00504 | 0.23648 | 0.95517 | 0.00370 | 0.04113 |
| 4 | 40 | 8.406 | 0.57825 | 0.00505 | 0.41670 | 0.95995 | 0.00299 | 0.03706 |
| 5 | 40 | 8.405 | 0.57998 | 0.00045 | 0.41957 | 0.96213 | 0.00027 | 0.03760 |

All patents and patent applications, test procedures (such as ASTM methods), and other documents cited herein are fully incorporated by reference to the extent such disclosure is not inconsistent with this invention and for all jurisdictions in which such incorporation is permitted.

When numerical lower limits and numerical upper limits are listed herein, ranges from any lower limit to any upper limit are contemplated.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

What is claim is:

1. A method for separating components of a mixture, the method comprising contacting an extractive agent with an azeotrope-like mixture, the mixture comprising at least one dissolved $C_4$-$C_7$ isoolefin monomer and a diluent comprising one or more hydrofluorocarbon(s), to form a stream of hydrofluorocarbon that is essentially free of the at least one dissolved monomer, wherein the ratio of the extractive agent to the diluent is from about 0.5:1 to about 1.0:0.2 on a molar basis, wherein the extractive agent comprises at least one hydrocarbon, wherein the at least one hydrocarbon comprises butane, pentane, methycyclopentane, isohexane, 2-methylpentane, 3-methylpentane, 2-methylbutane, 2,2-dimethylbutane, 2,3-dimethylbutane, 2-methylhexane, 3-methylhexane, 3-ethykentane, 2,2-dimethylpentane, 2,3-dimethylpentane, 2,4-dimethylpentane, 3,3-dimethylpentane, 2-methylheptane, 3-ethylhexane, 2,5-dimethylhexane, 2,2,4,-trimethylpentane, octane, heptane, , nonane, decane, dodecane, undecane, hexane, cyclopropane, cyclobutane, cyclopentane, , 1,1-dimethylcyclopentane, cis 1,2-dimethylcyclopentane, trans-1,2-dimethylcyclopentane, trans-1,3-dimethylcyclopentane, ethylcyclopentane, cyclohexane, methylcyclohexane, or mixtures thereof and wherein the hydrofluorocarbon(s) is represented by the formula: $C_xH_yF_z$ wherein x is an integer from 1 to 6 and y and z are integers of one or more.

2. The method of claim 1, wherein the mixture is a reactor effluent.

3. The method of claim 1, wherein the mixture is an azeotropic mixture.

4. The method of claim 1, wherein the hydrocarbon comprises hexane, heptane, and mixtures thereof.

5. The method of claim 1, wherein the $C_4$-$C_7$ isoolefin is isobutylene.

\* \* \* \* \*